(12) United States Patent
Leysen et al.

(10) Patent No.: US 6,552,011 B1
(45) Date of Patent: Apr. 22, 2003

(54) (ANDROST-5-EN-17BETA -YL)ALKYL SULFOXIDES AND SULFONES AND THEIR USE FOR CONTROL OF FERTILITY

(75) Inventors: Dirk Leysen, Lommel (BE); Jaap van der Louw, Oss (NL); Anja Wiersma, HE Elst (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/913,932

(22) PCT Filed: Feb. 25, 2000

(86) PCT No.: PCT/EP00/01558

§ 371 (c)(1),
(2), (4) Date: Aug. 20, 2001

(87) PCT Pub. No.: WO00/51618

PCT Pub. Date: Sep. 8, 2000

(30) Foreign Application Priority Data

Mar. 2, 1999 (EP) ............................... 99200572

(51) Int. Cl.[7] ........................ A61K 31/56; A01N 25/00; C07J 41/00; C07J 9/00
(52) U.S. Cl. ........................ 514/182; 514/843; 514/841; 552/520; 552/555
(58) Field of Search ................................ 514/182, 843, 514/841; 552/520, 555

(56) References Cited

FOREIGN PATENT DOCUMENTS

| DE | 247 008 A | 6/1987 |
| DE | 272 854 A | 10/1989 |
| DE | 282 230 A | 9/1990 |
| EP | 0 063 678 A | 11/1982 |
| WO | WO 98 28323 A | 7/1998 |
| WO | WO 98 52965 A | 11/1998 |
| WO | WO 98 55498 A | 12/1998 |

OTHER PUBLICATIONS

Shimada K. et al.: "Characterization of (24R)–24,25–Dihydroxyvitamin D3 Monoglucuronides Formed From A Rat Liver Microsomal Fraction Using High–Performance Liquid Chromatography and Chromatography–Mass Spectrometry", Analytical Communications, vol. 35, No. 1, Jan. 1998, pp. 33–36.

Barton, D.H.R.: "Protection du système diénique d l'ergostérol par formation d'audduits urazoliques: action comparée de l'anhydride phénylséléninique ser les urazoles et l'ergostérol. Influence de la structure de l'adduit." Bull. Soc. Chim. Fr., No. 5, 1985, pp. 849–858.

Schrötter, E.: "An Improved Synthesis of (24R)–24,25 dihydroxyprovitamin D3" Synthesis, No. 3, 1990, pp. 193–195.

Bogoslovskii, N.A.: "Synthesis of (24R)–24,25–dihydroxyvitamin D3", ZH. Org. Khim., vol. 26, No. 11, 1990, pp. 2398–2411.

Primary Examiner—Russell Travers
Assistant Examiner—Shengjun Wang
(74) Attorney, Agent, or Firm—Mark W. Milstead

(57) ABSTRACT

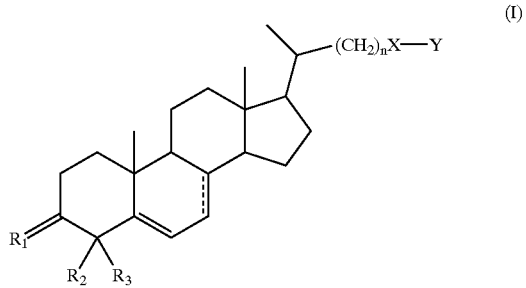

The invention relates to (androst-5-en-17beta-yl)alkylsulfoxides and sulfones having general formula (I), wherein R1, R2, R3, X and Y are defined in the specification. The compounds of the invention have meiosis inhibiting activity and can be used for the control of fertility.

8 Claims, No Drawings

(ANDROST-5-EN-17BETA-YL)ALKYL SULFOXIDES AND SULFONES AND THEIR USE FOR CONTROL OF FERTILITY

This application is a 371 of PCT/EP00/01558, filed Feb. 25, 2000, which claim the foreign priority of EPO 99200572.8, tiled Mar. 2, 1999.

The invention relates to (androst-5-en-17β-yl)alkyl sulfoxides and sulfones, to pharmaceutical compositions containing the same, as well as to the use: of these (androst-5-en-17β-yl)alkyl sulfoxides and sulfones for the preparation of a medicament for the control of fertility.

Sexual reproduction involves a cyclic alternation of diploid and haploid states: diploid cells divide by the process of meiosis to form haploid cells, and the haploid cells fuse in pairs at fertilization to form new diploid cells. The process of meiosis is characterized by two meiotic divisions, unique to both male and female germ cells. During the process two cell divisions, following one round of DNA replication, give rise to four haploid cells from one single diploid cell. Chromosomal crossover events, during which paternal and maternal genetic material is exchanged, occur during the prophase of the first meiotic division. At the end of the first meiotic division one member of each chromosome pair, composed of two sister chromatids is distributed to each daughter cell. The second meiotic division segregates each sister chromatide into a separate haploid cell. Male and female germ cells are subject to similar meiotic divisions but differ in the regulation of these processes. In the male meiosis is a continuous process in germ cells derived from a population of immature germ cells, the stem cell spermatogonia. After sexual maturation of the male, spermatogonia from this stem cell population embark on meiosis. The first and second meiotic division proceed without interruption and eventually give rise to four mature spermatozoa.

In the female, primary oocytes start the first meiotic division already during the embryonic stage but they remain arrested in the prophase (dictyate stage) until the female becomes sexually mature. Meiosis resumes at the time of ovulation (egg maturation) after which the first meiotic division is completed and the second meiotic division is initiated. In most vertebrates the second meiotic division is arrested at the metaphase and only completed after fertilization. At the end of the first and of the second meiotic division the cytoplasm divides asymmetrically to produce two secondary oocytes, each with a haploid number of single chromosomes, but greatly differing in size: one is a small polar body, which eventually degenerates, and the other is a large cell containing all the developmental potential. Finally one mature ovum is produced.

The stage at which the developing oocyte is released from the ovary and is ready for fertilization differs in different species. In both invertebrates and vertebrates ovarian accessory cells respond to polypeptides (gonadotropins) produced elsewhere in the body so as to control the maturation of the oocyte and eventually (in most species) ovulation. In humans the primary oocytes of the newborn female are arrested in prophase of meiotic division I and most are surrounded by a single layer of follicle cells; such an oocyte with its surrounding cells constitute the primordial follicle. A small portion of primordial follicles sequentially begins to grow to become developing follicles: the follicle cells enlarge and proliferate to form a multilayered envelope around the primary oocyte; the oocyte itself enlarges and develops the zona pellucida, an extracellular matrix consisting largely of glycoproteins, and cortical granules, specialized secretory vesicles just under the plasma membrane in the outer region, the cortex, of the egg cytoplasm [when the egg is activated by a sperm, these cortical granules release their contents by exocytosis; the contents of the granules act to alter the egg coat so as to prevent other sperms from fusing with the egg].

The developing follicles grow continuously and some of them develop a fluid-filled cavity, or antrum, to become antral follicles. Development of such follicles is dependent on gonadotropins (mainly follicle stimulating hormone –FSH) secreted by the pituitary gland and on estrogens secreted by the follicle cells themselves. Starting at puberty, a surge of secretion by the pituitary of another gonadotropin, luteinizing hormone (LH), activates a single antral follicle to complete its development: the enclosed primary oocyte matures to complete the meiotic division I as the stimulated follicle rapidly enlarges and ruptures at the surface of the ovary, releasing the secondary oocyte within. As is the case with most mammals, the secondary oocyte is triggered to undergo division II of meiosis only if it is fertilized by a sperm.

Studies on the mechanisms controlling initiation and regulation of the meiotic process in male and female germ cells suggest a role for cyclic nucleotides in mediating meiotic arrest. Spontaneous maturation of oocytes can be prevented by compounds that maintain elevated cAMP levels [Eppig, J. and Downs, S. (1984) *Biol. Reprod.* 30: 1–11]. Purines, like adenosine or hypoxanthine, are thought to be involved in the cAMP mediated maintenance of meiotic arrest [Eppig, J., Ward-Bailey, P. and Coleman, D. (1985) *Biol. Reprod.* 33: 1041–1049]. The presence of a meiosis regulating substance in a culture system of fetal mouse gonads was first described by Byskov, A. et al (1976) *Dev. Biol.* 52: 193–200. It was suggested that the concentrations of a meiosis activating substance (MAS) and a meiosis preventing substance (MPS) regulate the meiotic process in concert [Byskov, A. et al. (1994). In "The physiology of reproduction", Eds. Knobil, E. and Neill, J., Raven Press, New York]. More recently (3β,5β,20R)-4,4-dimethylcholesta-8,14,24-trien-3-ol (FF-MAS), isolated from human follicular fluid, and (3β,5α,20R)-4,4-dimethylcholesta-8,24-dien-3-ol, isolated from bull testes, were identified by Byskov, A. et al [(1995), *Nature* 374: 559–562] as endogenous meiosis activating substances in human and bovine, respectively. These sterols proved to be able to activate the resumption of meiosis in cultured cumulus enclosed and naked mouse oocytes.

Derivatives of the endogenous sterols, having either a saturated or an unsaturated cholestane side chain, have been disclosed in the international patent application WO98/28323 (NOVO NORDISK A/S) as meiosis inhibiting substances. Meiosis inhibiting substances are compounds that are antagonists of a naturally occurring meiosis activating substance. Thus, they could be used for contraception. A drawback of the compounds described in this patent application is that they are prone to rapid deactivation in the body [Hall, P. F. (1985) *Vitamins and Hormones*, 42: 315], thereby restricting their therapeutic potential as fertility control agents.

A need therefore exists for inhibitors of the meiotic process having improved in vivo activity.

To this end, the invention provides a group of compounds which has been found to possess this quality. It has thus been found that certain (androst-5-en-17β-yl)alkyl sulfoxides and sulfones show improved meiosis inhibiting activity.

Accordingly, the invention resides in the use of (androst-5-en-17β-yl)alkyl sulfoxides and sulfones having the general formula I given below, or a prodrug thereof, or a pharmaceutically acceptable salt thereof, for manufacturing a medicament for the control of fertility.

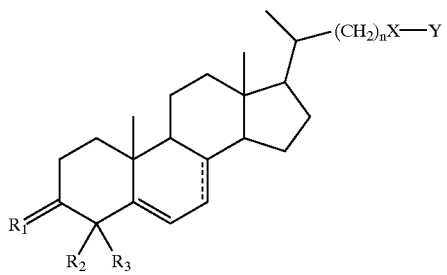

Formula I wherein
$R_1$ is (H,OR), (H,OSO$_3$H) or NOR; with R being H, (C$_{1-6}$)alkyl or (C$_{1-6}$)acyl;
each of $R_2$ and $R_3$ is independently hydrogen or (C$_{1-6}$) alkyl;
n is 0, 1, 2 or 3;
X is S(O) or S(O)$_2$;
Y is —CH$_2$—CR$_4$=CR$_5$R$_6$, wherein each of $R_4$, $R_5$ and $R_6$ is independently hydrogen, phenyl, halogen or (C$_{1-4}$)alkyl, optionally substituted by hydroxy, (C$_{1-4}$)alkoxy, oxo or halogen; or $R_4$ and $R_5$ together with the carbon atoms to which they are bound form a (C$_{5-6}$)cycloalkene ring; or $R_5$ and $R_6$ together with the carbon atom to which they are bound form a (C$_{3-6}$)cycloalkane ring; or
Y is —CH=CR$_7$—CR$_8$R$_9$R$_{10}$, wherein each of $R_7$, $R_8$ and $R_9$ is independently hydrogen, phenyl or (C$_{1-4}$) alkyl, optionally substituted by hydroxy, (C$_{1-4}$)alkoxy, oxo or halogen; $R_{10}$ is hydrogen, hydroxy or fluorine; or $R_7$ and $R_8$ together with the carbon atoms to which they are bound form a (C$_{3-6}$)cycloalkane ring; or $R_8$ and $R_9$ together with the carbon atoms to which they are bound form a (C$_{3-6}$)cycloalkane ring; or
Y is —CH$_2$—C≡CR$_{11}$, wherein $R_{11}$ is hydrogen or (C$_{1-4}$)alkyl, optionally substituted by hydroxy, (C$_{1-4}$) alkoxy, oxo or halogen; or $R_{11}$, is phenyl, optionally substituted by hydroxy, (C$_{1-4}$)alkoxy, (C$_{1-4}$)alkyl or halogen; or
Y is phenyl, optionally substituted by hydroxy, (C$_{1-4}$) alkoxy, (C$_{1-4}$)alkyl or halogen; and the dotted line indicates an optional additional bond.

The invention also resides in a method of treatment, comprising the administration to a human female of childbearing age, or to a fertile human male, of a medicament for the control of fertility, wherein said medicament comprises a (androst-5-en-17β-yl)alkyl sulfoxide or sulfone having the above general formula I (or a produg thereof or a pharmaceutically acceptable salt thereof).

The compounds used according to this invention have not been known before as having meiosis-inhibiting activity, or for any other capacity indicating their usefulness in the control of fertility. Many of these compounds being novel per se, the invention also resides in the above compounds, i.e. (androst-5-en-17β-yl)alkyl sulfoxides and sulfones having the above formula I or a pharmaceutically acceptable salt thereof, with the proviso that those compounds which incidentally have been known are excluded, said compounds being:
(3β,20S)-20-methyl-21-(phenylsulfonyl)pregna-5,7-dien-3-ol, which is known from DD 247008, and DD 282230;
(3β,20S)-20-methyl-21-(phenylsulfonyl)pregna-5,7-dien-3-ol acetate, which is known from DD 272854 and DD 282230;
(3β,20S)-20-methyl-21-(phenylsulfonyl)pregna-5,7-dien-3-ol benzoate, which is known from DD 282230;
[3β,20S,(21S)]-4,4,20-trimethyl-21-[(2-methyl-2-propenyl)sulfinyl]pregn-5-en-3-ol which is known as a by-product from WO 98/55498.

The invention further resides in a pharmaceutical composition comprising a (androst-5-en-17β-yl)alkyl sulfoxide or sulfone having the general formula I. Pharmaceutical compositions which comprise the disclaimers are within the ambit of the present invention.

The term (C$_{1-6}$)alkyl as used in the definition of formula I means a branched or unbranched alkyl group having 1–6 carbon atoms, like hexyl, pentyl, butyl, isobutyl, tertiary butyl, propyl, isopropyl, ethyl and methyl. Likewise, the term (C$_{1-4}$)alkyl means an alkyl group having 1–4 carbon atoms.

The term (C$_{3-6}$)cycloalkane ring means a cycloalkane ring having 3–6 carbon atoms, like cyclopropane, cyclobutane, cyclopentane and cyclohexane.

The term (C$_{5-6}$)cycloalkene ring means a cycloalkene ring having at least one double bond and 5 or 6 carbon atoms.

The term (C$_{1-6}$)acyl means an acyl group derived from a carboxylic acid having from 1–6 carbon atoms, like hexanoyl, pentanoyl, pivaloyl, butyryl, propanoyl, acetyl and formyl. Also included within the definition of (C$_{1-6}$)acyl are acyl groups derived from dicarboxylic acids, like hemi-glutaroyl, hemi-succinoyl, and hemi-maloyl. A preferred (C$_{1-6}$)acyl group is hemi-succinoyl.

The term (C$_{1-4}$)alkoxy means an alkyloxy having 1–4 carbon atoms, like butyloxy, propyloxy, isopropyloxy, ethyloxy, and, preferably, methyloxy.

The term halogen means F, Cl, Br or I. When halogen is a substituent at an alkyl group, like in the definition of $R_{4-9}$ and $R_{11}$, Cl and F are preferred, F being most preferred.

It is understood that the (androst-5-en-17β-yl)alkyl sulfoxides and sulfones of the invention have the natural configurations 8β, 9α, 10β, 13β, 14α, 17β. Preferred compounds according to the invention are the (androst-5-en-17β-yl)alkyl sulfoxides and sulfones of formula I wherein n is 0 or 1. More preferred are the comrpounds wherein in addition $R_1$ is (H,OR), wherein R has the previously given meaning, and the dotted line indicates a saturated bond. Among these preferred compounds those with the 3-OR substituent in the β-configuration are especially preferred. The configuration at position 20 of the (androst-5-en-17β-yl)alkyl sulfoxides and sulfones of the invention can be either R or S. Specifically preferred compounds of the invention are [3β,20S,(21R)]-4,4,20-trimethyl-21-[(2-methyl-2-propenyl) sulfinyl]pregn-5-en-3-ol and [3β,20S,(21R]-4,4,20-trimethyl-21 -(phenylsulfinyl) pregn-5-en-3-ol.

The meiosis inhibiting activity of the (androst-5-en-17β-yl)alkyl sulfoxides and sulfones of the invention is measured in an in vitro oocyte assay as the ability to inhibit the FF-Mas or 22S-hydroxy-FF-Mas induced maturation, in hypoxanthine media, in denuded oocytes (DO) or cumulus enclosed oocytes (CEO), respectively. The compounds can be used to inhibit meiosis in both male and female and thus can be used as contraceptive agents.

(Androst-5-en-17β-yl)alkyl sulfoxides and sulfones of the invention can be used for female contraception by inhibition of the naturally induced oocyte mraturation a caused by the gonadotrophin surge. These compounds lead to the ovulation of an immature oocyte which cannot be fertilized.

For male contraception the compounds of the invention can be administered to inhibit the spermatogenesis.

The (androst-5-en-17β-yl)alkyl sulfoxides and sulfones of this invention have the natural configurations 8β, 9α, 10β, 13β, 14α, 17β, and possess also one or more additional chiral carbon atoms. The compounds may therefore be obtained as a pure diastereomer, or as a mixture of diastereomers. Methods for obtaining the pure diastereomers are well known in the art, e.g. crystallization or chromatography.

Compounds according to formula I wherein X is S(O) may exist as a diastereoisomeric sulfoxide pair, due to the presence of the optically active sulfur atom. Both the diastereoisomeric mixture and the separate isomers are included in the present invention.

For therapeutic use, salts of the compounds of formula I are those wherein the counterion is pharmaceutically acceptable. However, salts of the acids according to formula I [i.e. compounds wherein $R_1$ is $(H,OSO_3H)$] may also find use, for example, in the preparation or purification of a pharmaceutically acceptable compound. All salts, whether pharmaceutically acceptable or not, are included within the ambit of the present invention. Examples of salts of acids according to the invention are mineral salts such as sodium salt, potassium salt, and salts derived from organic bases like ammonia, imidazole, ethylenediamine, triethylamine and the like.

The compounds of formula I or a pharmaceutically acceptable salt thereof, also referred to herein as the active ingredient, may be administered enterally or parenterally. The exact dose and regimen of administration of the active ingredient, or a pharmaceutical composition thereof, will necessarily be dependent upon the therapeutic effect to be achieved (e.g. female contraception or male contraception), and will vary with the particular compound, the route of administration, and the age and condition of the individual subject to whom the medicament is to be administered.

In general parenteral administration requires lower dosages than other methods of administration which are more dependent upon adsorption. However, a dosage for humans preferably contains 0.0001–25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

In case of in vitro or ex vivo applications, the compounds of the inventions are to be used in the incubation media in a concentration of approximately 0.01–5 μg/ml.

The present invention thus also relates to pharmaceutical compositions comprising a (androst-5-en-17β-yl)alkyl sulfoxide or sulfone according to formula I in admixture with pharmaceutically acceptable auxiliaries, and optionally other therapeutic agents. The auxilliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration. The compositions may be prepared by any method well known in the art of pharmacy, for example, using methods such as those described in Gennaro et al., Remington's Pharmaceutical Sciences (18th ed., Mack Publishing Company, 1990, see especially Part 8: Pharmaceutical Preparations and Their Manufacture). Such methods include the step of bringing in association the active ingredient with any auxilliary agent. The auxilliary agent(s), also named accessory ingredients, include those conventional in the art (Gennaro, supra), such as, fillers, binders, diluents, disintegrants, lubricants, colorants, flavoring agents and wetting agents.

Pharmaceutical compositions suitable for oral administration may be presented as discrete dosage units such as pills, tablets or capsules, or as a powder or granules, or as a solution or suspension. The active ingredient may also be presented as a bolus or paste. The compositions can further be processed into a suppository or enema for rectal administration.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example, water prior to use.

Compositions, or formulations, suitable for administration by nasal inhalation include fine dusts or mists which may be generated by means of metered dose pressurised aerosols, nebulisers or insufflators.

The (androst-5-en-17β-yl)alkyl sulfoxides and sulfones of the invention can also be administered in the form of implantable pharmaceutical devices, consisting of a core of active material, encased by a release rate-regulating membrane. Such implants are to be applied subcutaneously or locally, and will release the active ingredient at an approximately constant rate over relatively large periods of time, for instance from weeks to years. Methods for the preparation of implantable pharmaceutical devices as such are known in the art, for example as described in European Patent 0,303,306 (AKZO N.V.).

The compounds of the invention may be produced by various methods known in the art of organic chemistry in general, and especially in the art of the chemistry of steroids (see, for example: Fried, J. and Edwards, J. A., "Organic Reactions in Steroid Chemistry", Volumes I and II, Van Nostrand Reinhold Company, New York, 1972). A suitable method for the preparation of compounds of formula I is the reaction of a compound of general formula II,

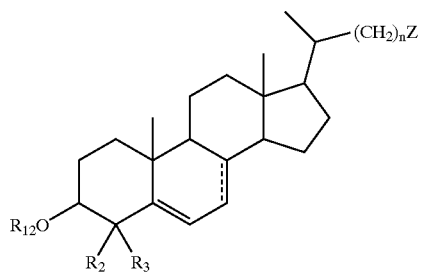

Formula II wherein $R_2$ and $R_3$ have the previously given meaning, $R_{12}$ is a hydroxy-protecting group such as an acyl group, like an acetyl group, a benzoyl group or a pivaloyl group, or an alkoxyalkyl group, like an ethoxyethyl group or a tetrahydropyranyl (THP) group, n is 0, 1, 2 or 3, and wherein Z is a halogen, preferably bromide or iodide, or a leaving group like tosyloxy or mesyloxy, and the dotted line indicates an optional bond, with a 2-propenyl mercaptan, a 2-propynyl mercaptan or a thiophenol derivative, or the reaction of a compound according to formula II wherein Z is SH, with a 2-propenyl chloride, bromide or iodide, or a 2-propynyl chloride, bromide or iodide, or with a 2-propenyl or 2-propynyl alcohol derivative wherein the hydroxy group is converted to a leaving group, such as mesyloxy or tosyloxy, whereafter a 17β-aryl(2-propenyl)(2-propynyl)thioalkyl-androst-5-ene derivative is oxidized to the corresponding sulfoxide [X=S(O)] or sulfone [X=S(O)$_2$] derivative, whereafter a 17β-(2-propenylsulfinyl)alkyl-androst-5-ene derivative or 17β-(2-propenylsulfonyl)alkyl-androst-5-ene derivative is optionally isomerized to the 17β-(1-propenylsulfinyl)alkyl-androst-5-ene derivative or 17β-(1-propenylsulfonyl)alkyl-androst-5-ene derivative, respectively, after which any remaining protecting groups are removed, and the 3-OH group of the product is optionally converted to a 3-OR group, wherein R has the meaning as previously defined, or wherein the 3-OH group is oxidized and the resulting 3-keto-group converted to NOR, wherein R has the meaning as previously defined.

The preparation of compounds having formula 11 is carried out using methods known in the art.

For instance, compounds of formula II (Z=OH, R$_{12}$=acyl) can be obtained from compounds having formula II (Z=OSit-BuMe$_2$, R$_{12}$=acyl), described in WO-09852965 and WO-09855498, by hydrolysis of the silyl ether.

Compounds of formula II (Z=OH) in which the 3-hydroxy function is protected as an alkoxyalkyl ether can be obtained from compounds of formula II (Z=OSit-BuMe$_2$, R$_{12}$=acyl) as follows: the ester function at C-3 is removed by reduction with lithium aluminium hydride, or by other hydride reducing agents known in the art, whereafter the 3-hydroxy group is reprotected as an alkoxyalkyl ether, e.g. an ethoxyethyl ether or a tetrahydropyranyl ether. Finally, treatment with a fluoride agent, e.g. potassium fluoride, tetrabutylammonium fluoride or other reagents known in the art then results in the formation of the unsaturated diol derivatives of formula II (Z=OH) in which the 3-hydroxy function is protected as an alkoxyalkyl ether. These and other suitable protective groups are known in the art, e.g. from Greene, T. W. and Wuts, P. G. M.: *Protective groups in Organic Synthesis*, Wiley, N.Y., 1991.

Compounds having formula II (Z=SH) are obtained from compounds of formula II (Z=OH) using methods known in the art (see e.g. Schoberl, A. et al, *Methoden der Organischen Chemie* (Houben-Weyl), Band IX, p. 7, Georg Thieme Publishers, Stuttgart, 1955). For instance, this conversion can be carried out by means of a Mitsunobu reaction with thioacetic acid followed by conversion to the thiol derivative by reduction or saponification [see Hughes, D. L., Organic Reactions 42, 335 (1992)]. Alternatively, they can be prepared by reaction of compounds of general formula II in which Z is a leaving group such as bromide, iodide, tosyloxy and mesyloxy, with thiourea followed by reaction with a base, like sodium hydroxide or potassium hydroxide [see e.g. Allewaert, K. et al, Bioorganic & Med. Chem. Lett. 3, 1859 (1993)].

The etherification reaction of compounds having formula II is carried out using methods known in the art.

For instance, compounds of formula I (X=S; Y=aryl, 2-propenyl, 2-propynyl) can be prepared by reaction of compounds of general formula II, wherein Z is a leaving group such as bromide, iodide, tosyloxy and mesyloxy, with a suitably substituted 2-propenyl mercaptan derivative, a 2-propynyl mercaptan derivative, or a thiophenol derivative, which is previously converted to the lithium, sodium or potassium salt [see e.g. Meerwein, H., *Methoden der Organischen Chemie* (Houben-Weyl), Band VI/3, p. 1, Georg Thieme Publishers, Stuttgart, 1965; Yin, J. et al, Tetrahedron Lett. 38, 5953 (1997) and references cited therein].

Compounds of formula I (X=S; Y=2-propenyl, 2-propynyl) can also be prepared analogously by means of an etherification reaction between a compound of formula II wherein Z is SH, which is previously converted to the lithium, sodium or potassium salt, with a suitably substituted 2-propenyl or 2-propynyl halide (Cl,Br,I) or with a suitably substituted 2-propenyl or 2-propynyl alcohol derivative in which the hydroxy group is converted to a leaving group, such as mesyloxy or tosyloxy.

Compounds of general formula I wherein X is S(O) or S(O)$_2$ can be prepared from compounds of formula I wherein X is S by oxidation using agents capable of converting a thio ether into a sulfoxide or a sulfone, e.g. sodium periodate, oxone, H$_2$O$_2$ and others [see e.g. Varma, R. S. et al, Tetrahedron Lett. 38, 6525 (1997) and references cited therein].

The isomerization of 17β-(2-propenylsulfinyl)alkyl-androst-5-ene derivatives or 17β-(2-propenylsulfonyl)alkyl-androst-5-ene derivatives to the 1-propenyl derivatives can be carried out with base, e.g. potassium tert-butoxide, sodium ethoxide, and others [see e.g. Svata, V. et al, Collect. Czech. Chem. Commun. 2619 (1978); Kimmelma, R., Acta Chem. Scand. 47, 1201 (1993); Maercker, A. Et al, J. Organomet. Chem. 116,21 (1976)].

Compounds of general formula I [X=S(O)$_2$; n=1,2,3] can also be prepared directly by reaction of compounds of general formula II in which Z is a leaving group such as bromide, iodide, tosyloxy and mesyloxy, with an unsubstituted or suitably substituted benzenesulfinic acid derivative, which is previously converted to the sodium or potassium salt [see Trost, B. M. et al, J. Am. Chem. Soc. 105, 5075 (1983)].

Compounds of formula I in which R$_1$ is (H,OH) may serve as starting material for the synthesis, using methods known in the art, of compounds of formula I in which R$_1$ is (H,OR), (H,OSO$_3$H) or NOR, and R is H, (C$_{1-6}$)alkyl, or (C$_{1-6}$)acyl.

The invention is further illustrated by the following examples.

EXAMPLE 1

[3β,20S,(21R)]-4,4,20-Trimethyl-21-[(2-methyl-2-propenyl)sulfinyl]pregn-5-en-3-ol (a) and [3β,20S,(21S)]-4,4,20-trimethyl-21-[(2-methyl-2-propenyl)sulfinyl]pregn-5-en-3-ol (b)

i)—Pyridinium p-toluenesulfonate (0.31 g) was added to a solution of (3β,20S)-21-[[(1,1-dimethylethyl)dimethylsilyl]oxy]-4,4,20-trimethylpregn-5-en-3-ol (WO9852965; 7.28 g) in dichloromethane (50 ml) and ethyl vinyl ether (20 ml). After stirring of the reaction mixture for 6 h at room temperature it was poured into a saturated aqueous solution of sodium hydrogencarbonate. The product was extracted into dichloromethane; the combined organic phases were washed with brine, dried over sodium sulfate, and concentrated under reduced pressure to give (3β,20S)-21-[[(1,1-dimethylethyl)dimethylsilyl]oxy]-3-[(1-ethoxyethyl)oxy]-4,4,20-trimethylpregn-5-ene (8.19 g), which was used in the following step without further purification.

ii)—A solution of the product obtained in the previous step (8.19 g) in a solution of tetrabutylammonium fluoride in tetrahydrofuran (1 M, 35 ml) was stirred at room temperature for 5 h. The reaction mixture was poured into a saturated aqueous solution of sodium hydrogencarbonate and the product was extracted into ethyl acetate. The combined organic phases were washed with water and brine, dried over sodium sulfate and concentrated under reduced pressure. Column chromatography afforded (3β,20S)-3-[(1-ethoxyethyl)oxy]-4,4,20-trimethylpregn-5-en-21-ol (5.17 g).

iii)—p-Toluenesulfonic anhydride (7.50 g) was added to a solution of the alcohol obtained in the previous step (5.17 g) in dry pyridine (45 ml). The reaction mixture was stirred at room temperature for 2 h and then poured into water (200 ml). After 30 min. stirring, a saturated aqueous solution of sodium hydrogencarbonate was added and the product was extracted into ethyl acetate. The combined organic phases were washed with brine, dried over sodium sulfate and concentrated under reduced pressure to give (3β,20S)-3-[(1-ethoxyethyl)oxy]-4,4,20-trimethyl-21-[[(4-methylphenyl)sulfonyl]oxyl]pregn-5-ene (6.50 g). The product was used in the following step without further purification.

iv)—Thiourea (3.36 g) was added to a solution of the tosylate obtained in the previous step (6.50 g) in dry dimethyl sulfoxide (56 ml) and the mixture was heated at 50–60° C. for 3 h. 3-Chloro-2-methyl-1-propene (4.42 ml) and powdered potassium hydroxide (4.06 g) were added and stirring was continued at 50–60° C. for 5 h. The mixture was poured into water and the product was extracted into ethyl acetate. The combined organic phases were washed with water, a saturated aqueous solution of sodium hydrogencarbonate and brine, dried over sodium sulfate and concentrated under reduced pressure, to give (3β,20S)-3-[(1-ethoxyethyl)oxy]-4,4-dimethyl-23-thiacholesta-5,25-diene (5.0 g) which was used in the following step without further purification.

v)—A solution of the product obtained in the previous step (5.0 g) in acetone (100 ml) was treated with a 4 M aqueous solution of hydrochloric acid (5 ml). The reaction mixture was stirred for 2 h at room temperature and subsequently poured into a saturated aqueous solution of sodium hydrogencarbonate. The acetone was removed under reduced pressure and the product was extracted into ethyl acetate. The combined organic phases were washed with brine, dried over sodium sulfate and concentrated under reduced pressure. Column chromatography afforded (3β,20S)-4,4-dimethyl-23-thiacholesta-5,25-dien-3-ol (1.46 g).

vi)—Hydrogen peroxide (30%, 0.51 ml) was added to a solution of the product obtained in the previous step (1.08 g) and trifluoroacetone (0.045 ml) in dichloromethane (13 ml). After 6 h stirring at room temperature, the reaction mixture was poured into a saturated aqueous solution of sodium thiosulfate. The product was extracted into ethyl acetate. The combined organic phases were washed with a saturated aqueous solution of sodium thiosulfate and with brine, dried over sodium sulfate and concentrated under reduced pressure, to give a 1:1 mixture of sulfoxides (1.07 9). Column chromatography and crystallization of a part of this material (0.77 g) afforded [3β,20S,(21R)]-4,4,20-trimethyl-21-[(2-methyl-2-propenyl)sulfinyl]pregn-5-en-3-ol (0.134 g), m.p. 199–204° C., and [3β,20S,(21S)]-4,4,20-trimethyl-21-[(2-methyl-2-propenyl)sulfinyl]pregn-5-en-3-ol (0.135 g), m.p. 193–202° C.

EXAMPLE 2

(3β,20S)-4,4,20-Trimethyl-21-[(2-methyl-2-propenyl)sulfonyl]pregn-5-en-3-ol

Oxone (0.90 g) was added to a solution of a mixture of [3β,20S,(21R)]-4,4,20-trimethyl-21-[(2-methyl-2-propenyl) sulfinyl]pregn-5en-3-ol and [3β,20S,(21S)]-4,4,20-trimethyl-21-[(2-methyl-2-propenyl)sulfinyl]pregn-5-en-3-ol (Example 1, step vi; 0.27 g) in a mixture of dichloromethane (12 ml), methanol (12 ml) and water (3 ml). After 3 h stirring at room temperature, the reaction mixture was poured into a saturated aqueous solution of sodium thiosulfate. The product was extracted into diethyl ether. The combined organic phases were washed with a saturated aqueous solution of sodium thiosulfate and with brine, dried over sodium sulfate and concentrated under reduced pressure. Column chromatography afforded (3β,20S)-4,4,20-trimethyl-21-[(2-methyl-2-propenyl) sulfonylipregn-5-en-3-ol (0.15 g), m.p. 189° C.

EXAMPLE 3

[3β,20S,(21R)]-4,4,20-Trimethyl-21-(phenylsulfinyl)pregn-5-en-3-ol (a) and [3β,20S,(21S)]-4,4,20-trimethyl-21-(phenylsulfinyl)prean-5-en-3-ol (b)

i)—Following a procedure analogous to that described under v of Example 1, (3β,20S)-21-[[(1,1-dimethylethyl) dimethylsilyl]oxy]-4,4,20-trimethylpregn-5-en-3-ol benzoate (WO-09852965; 10.7 g) was converted to (3β,20S)-4,4,20-trimethylpregn-5-ene-3,21-diol 3-benzoate (7.70 g).

ii)—Following a procedure analogous to that described under iii of Example 1, (3β,20S)-4,4,20-trimethylpregn-5-en-3,21-diol 3-benzoate (5.00 g) was converted to (3β,20S)-4,4,20-trimethyl-21-[[(4-methylphenyl)sulfonyl]oxy]pregn-5-en-3-ol benzoate (6.32 g).

iii)—Sodium hydride (60%, 0.456 g) was added to a solution of the tosylate described in the previous step (6.32 g) in dry dimethylformamide (60 ml).

Thiophenol (1.22 ml) was added dropwise and the reaction mixture was stirred for 1 h at room temperature. The mixture was poured into a saturated aqueous solution of ammonium chloride and the product was extracted into ethyl acetate. The combined organic phases were washed with brine, dried over sodiurm sulfate and concentrated, to give (3β,20S)-4,4,20-trimethyl-21-(phenylthio)pregn-5-en-3-ol benzoate (6.58 g). The product was used in the next step without further purification.

iv)—Following a procedure analogous to that described under vi of Example 1, the product obtained in the previous step (4.78 g) was converted to a 1:1 mixture of [3β,20S,(21R)]-4,4,20-trimethyl-21-(phenylsulfinyl)pregn-5-en-3-ol benzoate and [3β,20S,(21S)]-4,4,20-trimethyl-21-(phenylsulfinyl)pregn-5-en-3-ol benzoate (4.39 g).

v)—Powdered potassium hydroxide (2.0 g) was added to a solution of the mixture of sulfoxides obtained in the previous step (4.39 g) in tetrahydrofuran (40 ml) and methanol (6 ml). The mixture was stirred for 1 h at room temperature and then poured into a saturated aqueous solution of ammonium chloride. The product was extracted into ethyl acetate; the combined organic phases were washed with brine, dried over sodium sulfate, and concentrated under reduced pressure. Column chromatography and crystallization afforded [3β,20S,(21R)]-4,4,20-trimethyl-21-(phenylsulfinyl)pregn-5-en-3-ol (0.435 g), m.p. 191–200° C., and [3β,20S,(21S)]-4,4,20-trimethyl-21-(phenylsulfinyl) pregn-5-en-3-ol (0.233 g), m.p. 218–220° C.

EXAMPLE 4

(3β,20S)-4,4,20-Trimethyl-21-(phenylsulfonyl) pregn-5-en-3-ol i)—Iodine (2.30 g) was added to a mixture of triphenylphosphine (2.50 g), imidazole (0.65 g) and dry dichloromethane (59 ml). After 10 min. stirring (3β,20S)-4,4,20-trimethylpregn-5-ene-3,21-diol 3-benzoate (Example 3, step i; 2.48 g); in dry dichloromethane (25 ml) was added and stirring was continued for 30 min. The reaction mixture was poured into a saturated aqueous solution of sodium thiosulfate and the product was extracted into dichloromethane. The combined organic phases were washed with a saturated aqueous solution of sodium hydrogencarbonate and brine, dried over sodium sulfate and concentrated. Column chromatography afforded (3β,20S)-21-iodo-4,4,20-trimethylpregn-5-en-3-ol benzoate (1.20 g).

ii)—Sodium benzenesulfinate (0.50 g) was added to a solution of the iodide obtained in the previous step (1.20 g) in dry dimethylformamide (10 ml). The reaction mixture was stirred at 75° C. for 1 h, cooled, and poured into water. The product was extracted into ethyl acetate; the combined organic phases were washed with water and brine, dried over sodium sulfate and concentrated, to give (3β,20S)-4,4,20-trimethyl-21-(phenylsulfonyl)pregn-5-en-3-ol benzoate (1.22 g). The product was used without further purification.

iii)—Following a procedure analogous to that described under step v of Example 3, the benzoate obtained in the previous step (1.22 g) was converted to the 3-hydroxy compound, to give after column chromatography and crystallization, (3β,20S)-4,4,20-trimethyl-21-(phenylsulfonyl)pregn-5-en-3-ol (0.154 g). M.p. 176–181° C.

EXAMPLE 5

THE OOCYTE ASSAY

General:

Oocytes arrested in meiosis contain diffused chromosomes which are surrounded by an intact nuclear envelope known as the germinal vesicle (GV). Upon reinitiation of meiosis by the midcycle gonadotropin surge, the chromosomes recondense and the GV breaks down (GVBD). In vivo, the oocyte is exposed to hypoxanthine (HX), which maintains the oocyte arrested in the meiotic prophase. This meiotic arrest can be mimicked in vitro by addition of hypoxanthine to the culture medium. The agonistic activity of meiosis activating substances is measured as the ability to overcome the hypoxanthine maintained meiotic arrest in denuded oocytes (DO) or cumulus enclosed oocytes (CEO), i.e. as the ability to induce meiotic resumption in vitro.

Natural resumption of meiosis can be mimicked in vitro by addition of FF-Mas or other agonists to the culture medium containing hypoxanthine. The antagonistic activity of the compounds is measured as the ability to inhibit the FF-Mas or 22S-hydroxy-FF-Mas induced oocyte maturation in denuded oocytes or cumulus enclosed oocytes, respectively, in vitro.

Isolation of cumulus enclosed oocytes:

Ovaries are obtained from immature female mice (B6D2-F1, strain C57BL×DBA). At the age of 19, 20 or 21 days the mice are injected subcutaneously with a single dose of 20 IU follicle stimulating hormone (Humegon, Organon, The Netherlands) in saline.

Forty-eight hours after follicle stimulating hormone injection mice are killed by cervical dislocation. The ovaries are removed, freed of extraneous tissue and placed in a multidish containing 0.5 ml preparation medium at 37° C. L-15 Leibovitz medium (Gibco, pH 7.3±0.1) supplemented with bovine serum albumin (3 mg.ml$^{-1}$), L-glutamine (0.23 mM), sodium pyruvate (2 mM) and hypoxanthine (4 mM) is used as preparation medium. The antral follicles of the ovaries are punctured under a dissecting microscope using two 27-gauge needles attached to two 1 ml syringes. Cumulus enclosed oocytes (CEO) of uniform size are selected with a mouth-controlled pipette and rinsed in 0,5 ml fresh preparation medium. About 20 CEO are obtained from one ovary.

Isolation of denuded oocytes:

Oocytes freed from cumulus cells, i.e. denuded oocytes (DO), are obtained by gently flushing CEO through a fine-bore mouth-controlled pipette. DO were collected in fresh MEM alpha medium, containing bovine serum albumin (3 mg.ml$^{-1}$), L-glutamine (0.23 mM), sodium pyruvate (2 mM) and hypoxanthine (4 mM), and washed twice before transfer to the test medium.

Experimental design:

The oocyte assay is performed in 3 blocks, each block represents the ovaries of one mouse (randomized block design). At t=0 DO or CEO of the first ovary of the first mouse, are spread over well 1 and 3 and oocytes of the second ovary over well 2 and 4 of a 4-well multidish containing 0.5 ml of culture medium to which a (androst-5-en-17β-yl)alkyl sulfoxide or sulfone of the invention is added in case of agonistic testing. In case of antagonistic testing, a (androst-5-en-17β-yl)alkyl sulfoxide or sulfone of the invention is added together with FF-Mas (DO assay) or 22S-hydroxy-FF-Mas (CEO assay) [first block]. In case of agonistic testing, culture medium was used as control; in case of antagonistic testing, culture medium containing FF-Mas (DO assay) or 22S-hydroxy-FF-Mas (CEO assay) was used as control. The same procedure is performed for the second and third mouse [block 2 and 3]. The culture medium used is MEM alpha medium (Gibco, pH 7.3±0.1) saturated with $CO_2$ and supplemented with bovine serum albumin (3 mg.ml$^{-1}$), L-glutamine (0.23 mM), sodium pyruvate (2 mM) and hypoxanthine (4 mM). In total, each control or test compound is tested on 30 oocytes (10 oocytes per block). At t=0 the number of oocytes with intact germinal vesicles (GV) or germinal vesicle break-down (GVBD) is counted under an inverted microscope with differential interference contrast equipment. Only oocytes with an intact GV are used in the experiment. Oocytes are cultured 22 hours at 37° C. in 100% humidified atmosphere with 5% $CO_2$ in air. At the end of the culture period the number of oocytes with GV or GVBD per group is counted. For statistical analysis the percentage germinal vesicle breakdown is calculated for each group in one block. These percentages are subjected to arcsin transformation, and differences between control and test compounds are analyzed by an ANOVA test for a randomized block design. Results are presented in Table I (agonistic effects) and II (antagonistic effects).

TABLE I

Percentage germinal vesicle breakdown (GVBD) in oocytes following culturing in the presence of test compounds in agonistic testing.

| Compound[1] | % GVBD DO assay exp.(control) |
|---|---|
| [3β,20S,(21R)]-4,4,20-trimethyl-21-[(2-methyl-2-propenyl)sulfinyl]pregn-5-en-3-ol (Example 1a) | 3(12) |
| [3β,20S,(21R)]-4,4,20-trimethyl-21-(phenylsulfinyl)-pregn-5-en-3-ol (Example 3a) | 4(12) |
| (3β,5α,20R)-4,4-dimethylcholesta-8,14,24-trien-3-ol (FF-Mas)[2] | 84(7) |
| (3β,5α,20S,22S)-4,4-dimethylcholesta-8,14,24-triene-3,22-diol (22S-hydroxy-FF-Mas) | 97(2) |

[1]Each compound was tested at a concentration of 5 μM.
[2]Tested at a concentration of 10 μM.

TABLE II

Percentage germinal vesicle breakdown (GVBD) in oocytes following culturing in the presence of test compounds and FF-Mas (DO assay) or 22S-hydroxy-FF-Mas (CEO assay) in antagonistic testing.

| Compound | % GVBD DO assay[1] exp.(control) | CEO assay[2] exp.(control) |
|---|---|---|
| [3β,20S,(21R)]-4,4,20-trimethyl-21-[(2-methyl-2-propenyl)sulfinyl]pregn-5-en-3-ol (Example 1a) | 14(84) | 9(96)[3] |
| [3β,20S,(21R)]-4,4,20-trimethyl-21-(phenylsulfinyl)-pregn-5-en-3-ol (Example 3a) | 4(84) | 34(96)[3] |
| (3β,20S,22R)-cholest-5-en-3-ol [reference compound, 22R-hydroxycholesterol (WO-98/28323)] | 38(89) | 52(89)[4] |

[1]Concentration of (3β,5α,20R)-4,4-dimethylcholesta-8,14,24-trien-3-ol (FF-Mas): 5 μM; concentration of compound tested: 5 μM.
[2]Concentration of (3β,5α,20S,22S)-4,4-dimethylcholesta-8,14,24-triene-3,22-diol (22S-hydroxy-FF-Mas): 5 μM.
[3]Concentration of compound tested: 1.0 μM.
[4]Concentration of compound tested: 2.5 μM.

What is claimed is:

1. A method for inhibiting meiosis in an animal, comprising administering an effective amount of a compound which is an androst-5-en-17β-yl)alkyl sulfoxide, a sulfone, a prodrug or a salt thereof, of a compound of

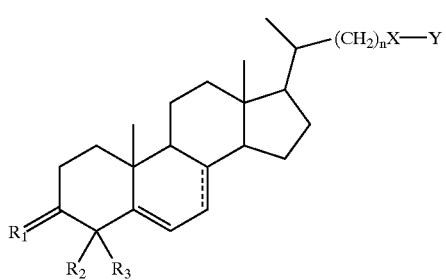

Formula I wherein $R_1$ is (H,OR), (H,OSO$_3$H) or NOR; with R being H, ($C_{1-6}$)alkyl or ($C_{1-6}$)acyl;

each of $R_2$ and $R_3$ is independently hydrogen or ($C_{1-6}$) alkyl;

n is 0, 1, 2 or 3; X is S(O) or S(O)$_2$;

Y is —CH$_2$—CR$_4$=CR$_5$R$_6$, wherein each of $R_4$, $R_5$ and $R_6$ is independently hydrogen, phenyl, halogen or ($C_{1-4}$)alkyl, optionally substituted by hydroxy, ($C_{1-4}$) alkoxy, oxo or halogen; or $R_4$ and $R_5$ together with the carbon atoms to which they are bound form a ($C_{5-6}$) cycloalkene ring; or $R_5$ and $R_6$ together with the carbon atom to which they are bound form a ($C_{3-6}$)cycloalkane ring; or Y is —CH=CR$_7$—CR$_8$R$_9$R$_{10}$, wherein each of $R_7$, $R_8$ and $R_9$ is independently hydrogen, phenyl or ($C_{1-4}$)alkyl, optionally substituted by hydroxy, ($C_{1-4}$) alkoxy, oxo or halogen; $R_{10}$ is hydrogen, hydroxy or fluorine; or $R_7$ and $R_8$ together with the carbon atoms to which they are bound form a ($C_{3-6}$)cycloalkane ring; or $R_8$ and $R_9$ together with the carbon atoms to which they are bound form a ($C_{3-6}$) cycloalkane ring; or Y is —CH$_2$—C≡CR$_{11}$, wherein $R_{11}$ is hydrogen or ($C_{1-4}$)alkyl, optionally substituted by hydroxy, ($C_{1-4}$) alkoxy, oxo or halogen; or $R_{11}$ is phenyl, optionally substituted by hydroxy, ($C_{1-4}$)alkoxy, ($C_{1-4}$)alkyl or halogen; or Y is phenyl, optionally substituted by hydroxy, ($C_{1-4}$)alkoxy, ($C_{1-4}$)alkyl or halogen; and the dotted line indicates an optional additional bond.

2. The method of claim 1, wherein the compound is an (androst-5-en-17β-yl)alkyl sulfoxide or sulfone and n is 0 or 1.

3. The method of claim 2, wherein the compound is an (androst-5-en-17β-yl)alkyl sulfoxide or sulfone and $R_1$ is (H,OR), wherein R is H or ($C_{1-6}$)acyl, the dotted line indicates a saturated bond, and the configuration of the 3-OR substituent is the β-configuration.

4. An (androst-5-en-17β-yl)alkyl sultoxide or sultone according to the general formula I:

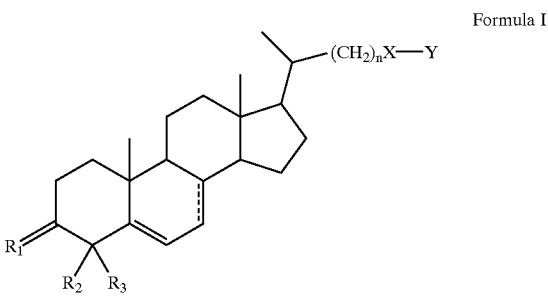

Formula I wherein $R_1$ is (H,OR), (H,OSO$_3$H) or NOR; with R being H, ($C_{1-6}$)alkyl or ($C_{1-6}$) acyl;

each of $R_2$ and $R_3$ is independently hydrogen or ($C_{1-6}$) alkyl;

n is 0, 1, 2 or 3; X is S(O) or S(O)$_2$;

Y is —CH$_2$—CR$_4$=CR$_5$R$_6$, wherein each of $R_4$, $R_5$ and $R_6$ is independently hydrogen, phenyl, halogen or ($C_{1-4}$)alkyl, optionally substituted by hydroxy, ($C_{1-4}$) alkoxy, oxo or halogen; or $R_4$ and $R_5$ together with the carbon atoms to which they are bound form a ($C_{5-6}$) cycloalkene ring; or $R_5$ and $R_6$ together with the carbon atom to which they are bound form a ($C_{3-6}$)cycloalkane ring; or Y is —CH=CR$_7$—CR$_8$R$_9$R$_{10}$, wherein each of $R_7$, $R_8$ and $R_9$ is independently hydrogen, phenyl or ($C_{1-4}$)alkyl, optionally substituted by hydroxy, ($C_{1-4}$) alkoxy, oxo or halogen; $R_{10}$ is hydrogen, hydroxy or fluorine; or $R_7$ and $R_8$ together with the carbon atoms to which they are bound form a ($C_{3-6}$)cycloalkane ring; or $R_8$ and $R_9$ together with the carbon atoms to which they are bound form a ($C_{3-6}$) cycloalkane ring; or Y is —CH$_2$—C≡CR$_{11}$, wherein $R_{11}$ is hydrogen or ($C_{1-4}$) alkyl, optionally substituted by hydroxy, ($C_{1-4}$)alkoxy, oxo or halogen; or $R_{11}$ is phenyl, optionally substituted by hydroxy, ($C_{1-4}$)alkoxy, ($C_{1-4}$)alkyl or halogen; or Y is phenyl, optionally substituted by hydroxy, ($C_{1-4}$) alkoxy, ($C_{1-4}$)alkyl or halogen; and the dotted line indicates an optional additional bond; or a pharmaceutically acceptable salt thereof, with the proviso that (3β,20S)-20-methyl-21-(phenylsulfonyl)pregna-5,7-diene-3-ol, (3β,20S)-20-methyl-21-(phenylsulfonyl) pregna-5,7-diene-3-ol acetate, (3β,20S)-20-methyl-21-(phenylsulfonyl)pregna-5,7-diene-3-ol benzoate, and ~3β,20S,(21S)])-4,4,20-trimethyl-21-[(2-methyl-2-propenyl)sulfinyl]pregna-5-ene-3-ol, are excluded, and when Y is phenyl, the dotted line is a saturated bond.

5. An (androst-5-en-17β-yl)alkyl sulfoxide or sulfone according to claim 4, characterized in that n is 0 or 1.

6. An (androst-5-en-17β-yl)alkyl sulfoxide or sulfone according to claim 5, characterized in that $R_1$ is (H,OR), wherein R is H or ($C_{1-6}$)acyl, the dotted line indicates a saturated bond, and the configuration of the 3-OR substituent is the β-configuration.

7. An (androst-5-en-17β-yl)alkyl sulfoxide or sulfone selected from the group consisting of ((3β,20S,(21R))-4,4,20-trimethyl-21-((2-methyl-2-propenyl)sulfinyl))pregn-5-en-3-ol, (3β,20S,(21R))-4,4,20-trimethyl-21-(phenylsulfinyl)pregn-5-en-3-ol, and salts thereof.

8. A pharmaceutical composition comprising an (androst-5-en-17β-yl)alkyl sulfoxide or sulfone according to claim 4, or a salt thereof, in admixture with one or more pharmaceutically acceptable auxiliaries.

* * * * *